US012708687B2

(12) United States Patent
Shah

(10) Patent No.: US 12,708,687 B2
(45) Date of Patent: Aug. 18, 2026

(54) METHOD AND A DEVICE FOR ENHANCED UV DISINFECTION

(71) Applicant: RAVIOR INC, Milford, NH (US)

(72) Inventor: Pratik Jitendrakumar Shah, Guelph (CA)

(73) Assignee: RAVIOR INC, Milford, NH (US)

( * ) Notice: Subject to any disclaimer, the term of this patent is extended or adjusted under 35 U.S.C. 154(b) by 1192 days.

(21) Appl. No.: 17/509,815

(22) Filed: Oct. 25, 2021

(65) Prior Publication Data

US 2022/0125980 A1 Apr. 28, 2022

Related U.S. Application Data

(60) Provisional application No. 63/105,337, filed on Oct. 25, 2020.

(51) Int. Cl.
*A61L 2/26* (2006.01)
*A61L 2/10* (2006.01)
*A61L 9/20* (2006.01)
*A61L 103/00* (2026.01)

(52) U.S. Cl.
CPC .................. *A61L 2/26* (2013.01); *A61L 2/10* (2013.01); *A61L 9/20* (2013.01); *A61L 2103/00* (2026.01); *A61L 2202/11* (2013.01)

(58) Field of Classification Search
CPC ..... A61L 2/26; A61L 2/10; A61L 9/20; A61L 2202/11; A61L 2202/20; A61L 2202/14; A61L 2202/25; A61L 2209/111; H05B 47/25; H05B 47/10
See application file for complete search history.

(56) References Cited

U.S. PATENT DOCUMENTS

| | | | | |
|---|---|---|---|---|
| 5,065,072 | A * | 11/1991 | Albou | H05B 41/2885 315/83 |
| 5,550,434 | A * | 8/1996 | King | H05B 41/2885 398/186 |
| 2012/0067864 | A1* | 3/2012 | Kusuda | H01L 21/67115 219/385 |
| 2020/0161069 | A1 | 5/2020 | Ramanand et al. | |
| 2022/0202317 | A1* | 6/2022 | Taghioskoui | A61B 10/04 |

FOREIGN PATENT DOCUMENTS

| | | | | |
|---|---|---|---|---|
| DE | 19643925 | A1 * | 5/1998 | H05H 1/2406 |
| JP | 2006324039 | A * | 11/2006 | |
| RU | 995391 | A1 * | 2/1983 | |

(Continued)

*Primary Examiner* — Regina M Yoo
(74) *Attorney, Agent, or Firm* — Oliff PLC

(57) ABSTRACT

The present disclosure describes a pulsed ultraviolet (PUV) device and method of operating the PUV device for enhanced UV disinfection. The method may comprise generating a plurality of charging commands during an operation cycle of the PUV device. In an aspect, generating the plurality of charging commands may comprise generating a plurality of variable voltage amplitudes for charging a capacitor provided in the PUV device. The plurality of variable voltage amplitudes comprises at least one voltage amplitude greater than a cut off voltage amplitude. The method may further comprise generating a plurality of discharging commands corresponding to the plurality of charging commands for discharging the capacitor to generate IN pulses across the germicidal lamp.

4 Claims, 7 Drawing Sheets

400

(56) References Cited

FOREIGN PATENT DOCUMENTS

| | | | | |
|---|---|---|---|---|
| RU | 2031659 C1 * | 3/1995 | | |
| RU | 2088286 C1 * | 8/1997 | | |
| RU | 2396092 C1 * | 8/2010 | ............... | A61L 9/20 |
| RU | 104070 U1 * | 5/2011 | | |

* cited by examiner 300-1

300-2

300-3

300-4

METHOD AND A DEVICE FOR ENHANCED UV DISINFECTION

TECHNICAL FIELD

The present disclosure generally relates to the technical field of disinfection using ultraviolet light, and in particular, to a method and device for enhanced ultraviolet (UV) disinfection.

BACKGROUND

Use of ultraviolet (UV) light for disinfection treatment of air, water, food, surfaces etc. is well known in the art. UV disinfection is a process of killing bacteria, protozoa, molds, algae, viruses, and other types of microorganisms using UV light generated by UV light sources. UV disinfection destroys the DNA of microorganisms which leaves them dead and unable to grow further. Specifically, UV light induces damage to genomes of microorganisms, breaking bonds and forming photo dimeric lesions in nucleic acids, DNA, and RNA. These lesions prevent both transcription and replication and ultimately lead to inactivation of the microorganisms.

Pulsed IN light disinfection is a novel disinfection technology that offers effective inactivation of microorganisms within a significantly short period of time. In a pulsed UV (PUV) device, pulsed energy from a germicidal lamp is imparted on the surfaces for a predefined operation cycle or disinfection cycle to kill the pathogens/microorganisms. However, it may not be possible to constantly deliver high energy pulses from the PUV device because maximum energy delivered by the PUV device is limited by an input current available from an input source (e.g., AC outlet) and increasing the input current beyond a safe limit may lead to overloading of circuit and eventually to tripping of a circuit breaker in mid of the operation cycle resulting in poor disinfection. To avoid the tripping and to achieve an intended disinfection, the PUV device is forced to run for multiple operation cycles of small durations or for longer operation cycles of low energy, thereby yielding a substandard operational performance.

In some scenarios, multiple devices/loads may share the same power line. For example, in a hospital room multiple devices may be connected to the same shared power line (or input source). The current available from the input source is divided among the various devices and the PUV device connected on the shared power line. Thus, in presence of other devices, the current available for the PUV device decreases leading to poor disinfection.

Thus, with the huge and rapidly growing demand of pulsed UV disinfection devices, there exists a need for further improvements in the existing technology, especially there exists a need to develop an enhanced PUV device that can run the entirety of the operation cycle without any interruptions while delivering high energy pulses.

The information disclosed in this background section is only for enhancement of understanding of the general background of the invention and should not be taken as an acknowledgement or any form of suggestion that this information forms the prior art already known to a person skilled in the art.

SUMMARY

One or more shortcomings discussed above are overcome, and additional advantages are provided by the present disclosure. Additional features and advantages are realized through the techniques of the present disclosure. Other embodiments and aspects of the disclosure are described in detail herein and are considered a part of the disclosure.

An objective of the present disclosure is to provide an enhanced pulsed ultraviolet (PUV) device that can run the entirety of an operation/disinfection cycle without any interruptions while delivering high energy pulses.

Another objective of the present disclosure is to reduce a disinfection time and improve efficacy of UV disinfection.

The above stated objects as well as other objects, features, and advantages of the present disclosure will become clear to those skilled in the art upon review of the following description, the attached drawings, and the appended claims.

In a non-limiting embodiment of the present disclosure, the present application discloses a method of operating a pulsed ultraviolet (PUV) device comprising a pulse generator and a germicidal lamp. The method may comprise generating a plurality of charging commands during an operation cycle of the PUV device where generating the plurality of charging commands may comprise generating a plurality of variable voltage amplitudes for charging a capacitor of the pulse generator, and where the plurality of variable voltage amplitudes comprises at least one voltage amplitude greater than a cut off voltage amplitude. The method may further comprise generating a plurality of discharging commands corresponding to the plurality of charging commands for discharging the capacitor to generate IN pulses across the germicidal lamp.

In another non-limiting embodiment of the present disclosure, the present application discloses a pulsed ultraviolet (PUV) device comprising a germicidal lamp and a controller electrically connected between an input source and the germicidal lamp. The controller may be configured to generate a plurality of charging commands during an operation cycle of the PUV device, where for generating the plurality of charging commands, the controller is configured to generate a plurality of variable voltage amplitudes for charging a capacitor of the pulse generator, and where the plurality of variable voltage amplitudes comprises at least one voltage amplitude greater than a cut off voltage amplitude. The controller may be further configured to generate a plurality of discharging commands corresponding to the plurality of charging commands for discharging the capacitor to generate IN pulses across the germicidal lamp.

In another non-limiting embodiment of the present disclosure, the present application discloses a non-transitory computer readable media storing one or more instructions executable by a controller electrically connected between an input source and a germicidal lamp. The one or more instructions may comprise one or more instructions for generating a plurality of charging commands during an operation cycle of the PUV device, where the one or more instructions for generating the plurality of charging commands comprises one or more instructions for generating a plurality of variable voltage amplitudes for charging a capacitor of the pulse generator, and where the plurality of variable voltage amplitudes comprises at least one voltage amplitude greater than a cut off voltage amplitude. The one or more instructions may further comprise one or more instructions for generating a plurality of discharging commands corresponding to the plurality of charging commands for discharging the capacitor to generate IN pulses across the germicidal lamp.

In another non-limiting embodiment of the present disclosure, the plurality of charging commands comprises n sets of charging commands, each set comprising at least one charging command, and where each set of the n sets of charging commands is associated with a particular charging interval and a particular voltage amplitude.

In another non-limiting embodiment of the present disclosure, a time interval between any two consecutive charging commands among the plurality of charging commands is same during the operation cycle, and a voltage amplitude associated with one set of charging commands is different from a voltage amplitude associated with another set of charging commands.

In another non-limiting embodiment of the present disclosure, a charging interval associated with one set of charging commands is different from a charging interval associated with another set of charging commands, and a voltage amplitude associated with one set of charging commands is different from a voltage amplitude associated with another set of charging commands.

In another non-limiting embodiment of the present disclosure, the operation cycle of the PUV device comprises n sub-operation cycles, and wherein each sub-operation cycle of the n sub-operation cycles comprises one or more charging commands having the same charging interval and the same voltage amplitude.

In another non-limiting embodiment of the present disclosure, the cut-off voltage is the voltage below which a circuit breaker electrically connected between an input source and the pulse generator does not trip.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF DRAWINGS

Further aspects and advantages of the present disclosure will be readily understood from the following detailed description with reference to the accompanying drawings. Reference numerals have been used to refer to identical or functionally similar elements. The figures together with a detailed description below, are incorporated in and form part of the specification, and serve to further illustrate the embodiments and explain various principles and advantages, in accordance with the present disclosure wherein:

FIG. 3(*b*) shows another exemplary graph 300-2 illustrating variations in voltage across a capacitor of the PUV device for performing IN disinfection, in accordance with some embodiments of the present disclosure.

FIG. 3(*c*) shows an exemplary graph 300-3 illustrating variations in voltage across a capacitor of the PUV device for performing UV disinfection, in accordance with some embodiments of the present disclosure.

FIG. 3(*d*) shows an exemplary graph 300-4 illustrating variations in voltage across a capacitor of the PUV device for performing UV disinfection, in accordance with some embodiments of the present disclosure

Figure 1:
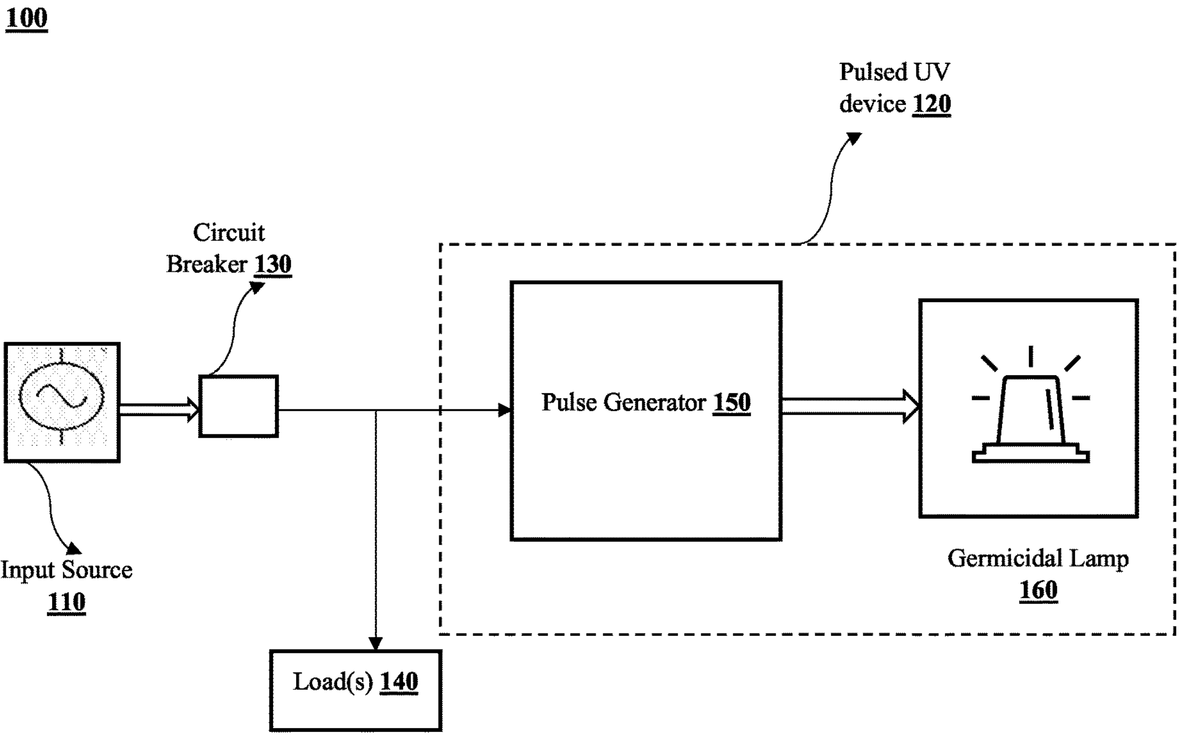
FIG. 1 shows an exemplary schematic of a system 100 of operating a pulsed ultraviolet (PUV) device, in accordance with some embodiments of the present disclosure.

It should be appreciated by those skilled in the art that any block diagrams herein represent conceptual views of the illustrative systems embodying the principles of the present disclosure. Similarly, it will be appreciated that any flowcharts, flow diagrams, state transition diagrams, pseudo code, and the like represent various processes which may be substantially represented in computer readable medium and executed by a computer or processor, whether or not such computer or processor is explicitly shown.

DETAILED DESCRIPTION

In the present document, the word "exemplary" is used herein to mean "serving as an example, instance, or illustration." Any embodiment or implementation of the present disclosure described herein as "exemplary" is not necessarily to be construed as preferred or advantageous over other embodiments.

While the disclosure is susceptible to various modifications and alternative forms, specific embodiments thereof have been shown by way of example in the drawings and will be described in detail below. It should be understood, however, that it is not intended to limit the disclosure to the particular form disclosed, but on the contrary, the disclosure is to cover all modifications, equivalents, and alternatives falling within the spirit and the scope of the disclosure.

The terms "comprise(s)", "comprising", "include(s)", or any other variations thereof, are intended to cover a non-exclusive inclusion, such that a setup, device, apparatus, system, or method that comprises a list of components or steps does not include only those components or steps but may include other components or steps not expressly listed or inherent to such setup or device or apparatus or system or method. In other words, one or more elements in a device or system or apparatus proceeded by "comprises . . . a" does not, without more constraints, preclude the existence of other elements or additional elements in the system.

The terms like "at least one" and "one or more" may be used interchangeably throughout the description. The terms like "a plurality of" and "multiple" may be used interchangeably throughout the description. Further, the terms like "operation cycle", "disinfection cycle" may be used interchangeably throughout the description. Further, the terms like "input source", "power source", and "AC outlet" may be used interchangeably throughout the description. Further, the terms like "cutoff voltage" and "cutoff voltage amplitude" may be used interchangeably throughout the description. Further, the terms like "waiting period" and "cooling period" may be used interchangeably throughout the description.

In the following detailed description of the embodiments of the disclosure, reference is made to the accompanying drawings that form a part hereof, and in which are shown by way of illustration of specific embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense. In the following description, well known functions or constructions are not described in detail since they would obscure the description with unnecessary detail.

In the present disclosure, the term 'disinfection' is used within the context of its broadest definition. The disinfection may refer to any process or technique of destroying or inhibiting the growth of microorganisms and/or pathogens at least using UV light. Further, in the present disclosure, the term 'pulsed ultraviolet (PUV) device' or 'PUV device' is used within the context of its broadest definition. The PUV device may refer to any device capable of providing UV light pulses of same or different energy levels for the purpose of disinfection.

Ultraviolet (UV) light disinfection may be implemented either using pulsed UV (PUV) light or continuous UV light. The pulsed UV light provides in-depth penetration into cells of microorganisms and induces thousand folds more instantaneous energy compared to continuous UV light. Further, a cooling period may be introduced between pulses in the pulsed UV light and hence tripping of circuits may be avoided. For these and other reasons, the PUV light is considered to be more effective than the continuous UV light for disinfection purposes. In a pulsed UV disinfection system, pulsed energy from a germicidal lamp is imparted on a subject to kill pathogens/microorganisms. The PUV light has a variety of applications including research applications (destruction of microorganisms); sanitization, decontamination and sterilization of surfaces, air, foods, and liquids etc.

The present disclosure provides techniques (methods and devices/apparatus/systems) for performing enhanced UV disinfection using the PUV light. As described in background section, it may not be possible to constantly deliver high energy pulses from a PUV device because maximum energy provided by the PUV device is limited by an input current available from an input source (e.g., AC outlet) and increasing the input current beyond a safe limit may lead to overloading of circuit and eventually leading to tripping of a circuit breaker in mid of an operation cycle, which results in poor disinfection and substandard operational performance.

To overcome these and other problems, the present disclosure proposes a PUV device and techniques of operating the same. The PUV device of the present disclosure comprises at least a pulse generator and a germicidal lamp. The pulse generator may generate a plurality of variable voltage amplitudes for charging a capacitor of the pulse generator during an operation cycle. At least one of the plurality of voltage amplitudes is kept high (greater than a cut off voltage amplitude) so as to deliver more energy output. Thus, the proposed techniques provide extremely high constant energy output for disinfecting the surfaces/water/air/food etc. that too without tripping circuit breakers. By providing the high constant energy output, the proposed techniques reduce the disinfection time and improve efficacy of disinfection.

Referring now to FIG. 1, which illustrates an exemplary schematic of a system 100 of operating a pulsed ultraviolet (PUV) device, in accordance with some embodiments of the present disclosure. The system 100 may comprise an input source 110, a pulsed ultraviolet (PUV) device 120, a circuit breaker 130 electrically connected between the input source 110 and the PUV device 120, and other devices 140 electrically connected at the output of the input source 110 between the circuit breaker 130 and the PUV device 120.

The input source 110 may be any voltage source already known in the art or developed later including, but not limited to, a battery, a generator, an alternator, AC power supply etc. In one non-limiting embodiment of the present disclosure, the input source 110 may supply an Alternating Current (AC) power signal to the PUV device 120 via the circuit breaker 130. The input source 110 may supply a predefined voltage to the PUV device 120. The other devices 140 may be any electrical appliances or loads already known in the art or developed later that consume electric power or energy.

The circuit breaker 130 is a device or component designed to protect an electrical circuit. The circuit breaker 130 may be operated automatically or manually for protecting the electrical circuit. The circuit breaker 130 is connected between the input source 110 and the PUV device 120 for continuously monitoring a current passing through it. When the current passing through the circuit breaker 130 exceeds a safe current limit, the circuit breaker 130 automatically trips or deactivates thereby interrupting the input current passing through it. For example, in the event of an overload, the circuit breaker 130 immediately shuts off the PUV device 120 by interrupting the input current.

In one non-limiting embodiment, the PUV device 120 may comprise at least a pulse generator 150 and a germicidal lamp 160. The pulse generator 150 may be configured to receive power from the input source 110 and generate pulsed UV signals for deriving the germicidal lamp 160. In general, a germicidal lamp produces ultraviolet C light for inactivating the microorganisms. In the present disclosure, the germicidal lamp 160 is configured to emit PUV light for the purpose of disinfecting. The germicidal lamp 160 may any suitable UV lamp already known in the art or developed later. In one embodiment, the germicidal lamp 160 may comprise one or more UV lamps.

In one non-limiting embodiment, the germicidal lamp 130 may be electrically connected with the pulse generator 150 using wired connections.

Figure 2:
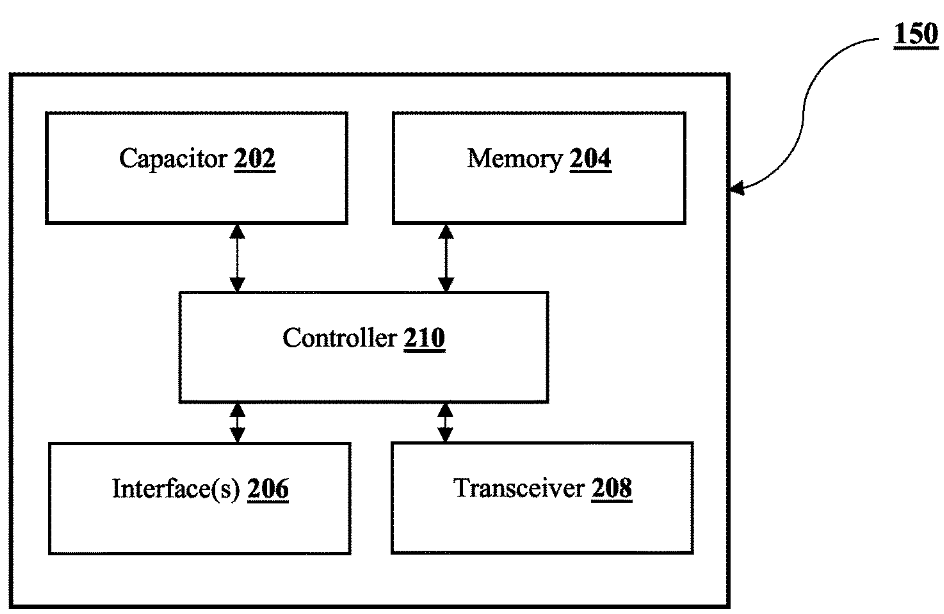
FIG. 2 shows a block diagram 200 of a UV pulse generator for performing UV disinfection, in accordance with some embodiments of the present disclosure.
Figure 3A:
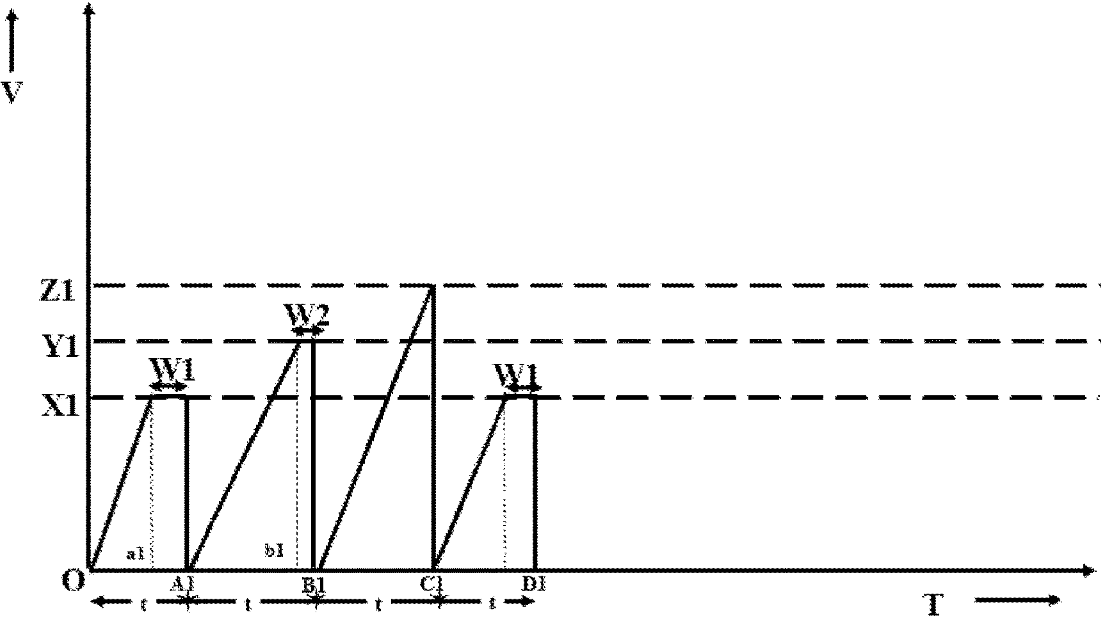
FIG. 3(*a*) shows an exemplary graph 300-1 illustrating variations in voltage across a capacitor of the PUV device for performing IN disinfection, in accordance with some embodiments of the present disclosure.
Figure 3B:
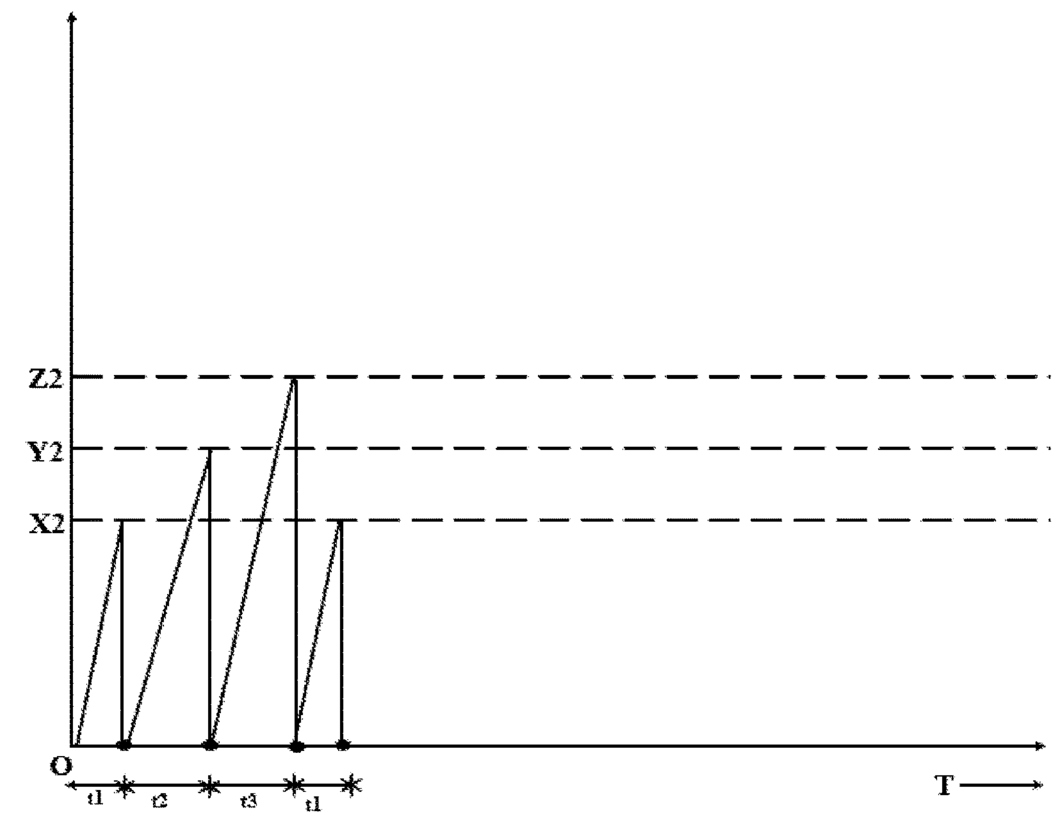
Figure 3C:
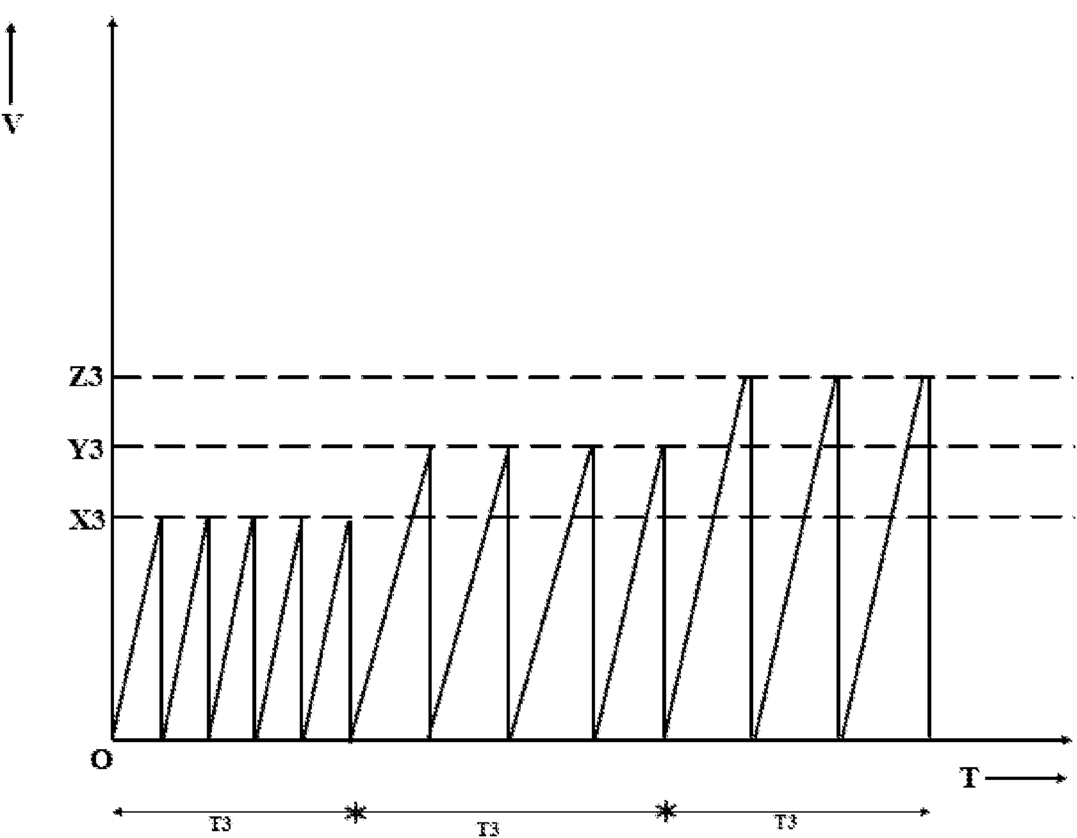
Figure 3D:
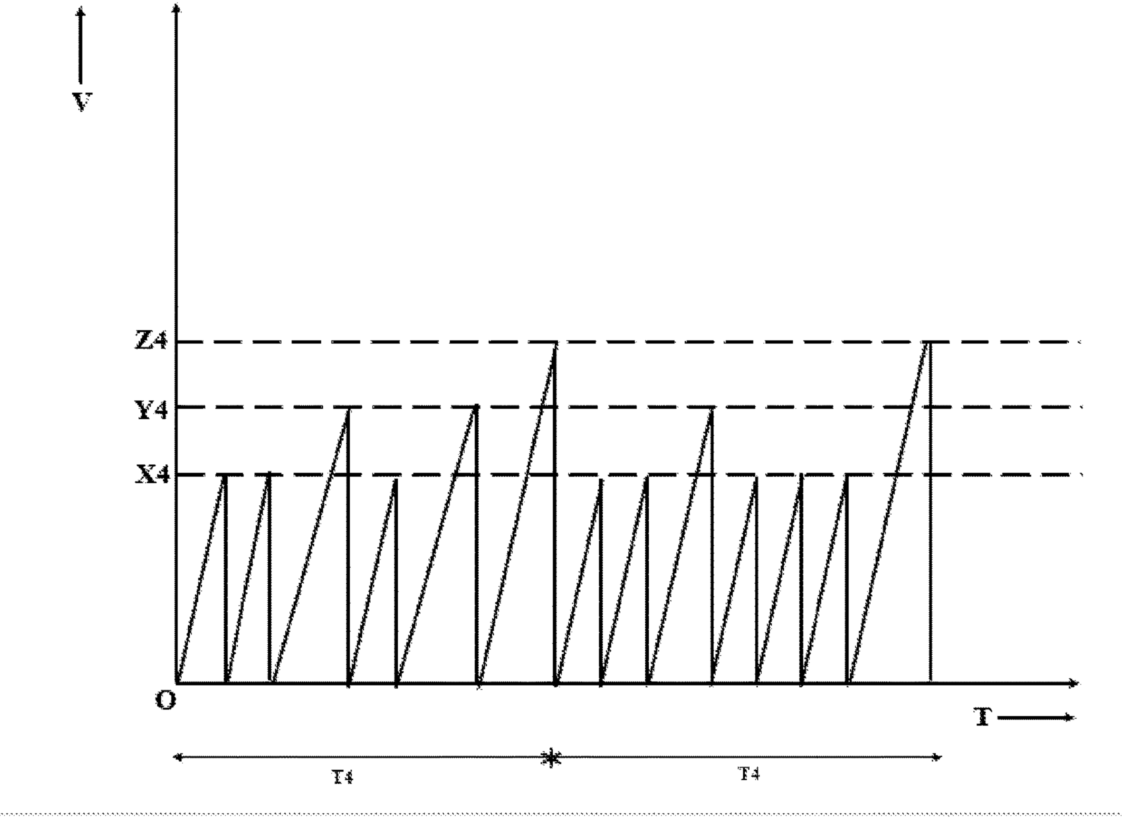

Referring now to FIG. 2, which is a block diagram 200 of the pulse generator 150 for generating pulsed UV signals for deriving the germicidal lamp 160, in accordance with some embodiments of the present disclosure. The pulse generator 150 of FIG. 2 may comprise at least one capacitor 202, memory 204, various interfaces 206, a transceiver 208, and at least one controller 210. The at least one controller 210 may be communicatively coupled with the capacitor 202, the memory 204, various interfaces 206, the transceiver 208.

The controller 210 may include, but not restricted to, a general-purpose processor, a Field Programmable Gate Array (FPGA), an Application Specific Integrated Circuit (ASIC), a Digital Signal Processor (DSP), microprocessors, microcomputers, micro-controllers, central processing units, state machines, logic circuitries, and/or any devices that manipulate signals based on operational instructions. A controller may also be implemented as a combination of computing devices, e.g., a combination of a DSP and a microprocessor, a plurality of microprocessors, one or more microprocessors in conjunction with a DSP core, or any other such configuration.

The memory 204 may be configured to store one or more instructions. The controller 210 may be configured to execute the one or more instructions stored in the memory 204. The memory 204 may include a Random-Access Memory (RAM) unit and/or a non-volatile memory unit such as a Read Only Memory (ROM), optical disc drive, magnetic disc drive, flash memory, Electrically Erasable Read Only Memory (EEPROM), a memory space on a server or cloud and so forth.

The interfaces 206 may a wired or wireless interface including a variety of software and hardware interfaces, for example, a web interface, a graphical user interface, an input device-output device (I/O) interface, a network interface, and the like. The I/O interfaces may allow the pulse generator 150 or the PUV device 120 to interact with other devices/components directly or through other devices. The transceiver 208 may allow the pulse generator 208 or the PUV device 120 to transmit various types of data/information to other devices and receive various types of data/information from the other devices.

The input source 110 supplies power to the pulse generator 150 via the circuit breaker 130. Consider that:

$P_i$—Input power provided by the input source 110

$V_i$—Input voltage across the circuit breaker 130

$I_i$—Input current across the circuit breaker 130

Assuming that there are no other devices/loads 140 connected at the input source, an input voltage and an input current across the pulse generator 150 is same as the input voltage $V_i$ and input current $I_i$ across the circuit breaker 130. The circuit breaker 130 has an associated current rating (i.e., the maximum amount of current that the circuit breaker 130 is designed to carry without tripping). In the present disclosure, the current rating is also referred to as a safe current or a cut off current represented as $I_{th}$.

The pulse generator 150 may include at least one capacitor 202 and the input voltage $V_i$ may be first converted into a DC voltage (V). The DC voltage (also referred as 'charging voltage' in the present disclosure) may be applied across the capacitor 202 for charging the capacitor 202. The controller 210 may adjust a voltage amplitude of the charging voltage to a desired voltage amplitude. The controller 210 may then generate a charging command for charging the capacitor 202 based on the adjusted voltage amplitude. Once the capacitor is charged, the controller 210 may then generate a discharging command for discharging the capacitor 202 to generate a pulsed energy signal which may be supplied to the germicidal lamp 160 to generate a UV pulse across the germicidal lamp 160. This process of charging and discharging may be repeated a number of times using different voltage amplitudes during the operation cycle to generate UV pulses across the germicidal lamp 160 for killing the pathogens/microorganisms.

Consider 'C' is the capacitance of the capacitor 202 and 'V' is the voltage amplitude across the capacitor 202 or the charging voltage of the capacitor 202. Then, the energy per pulse of the pulsed energy signal generated by the pulse generator 150 is given by:

$$E = \frac{1}{2}CV^2 \tag{1}$$

If 'f' is the frequency or pulse frequency (i.e., a number of pulses per second generated by the pulse generator 150), then, the energy per second generated by the pulse generator 150 is given by:

$$E = \frac{1}{2}CV^2 f \tag{2}$$

Total energy generated by the pulse generator for an operation cycle of T seconds is given by:

$$E = \frac{1}{2}CV^2 fT \tag{3}$$

To provide enhanced disinfection, it is desirable to keep the energy per second or per pulse high so as to keep the total energy high. According to equation (2), it is possible to increase the energy per second by increasing C (capacitance), V (charging voltage of the capacitor 202), or f (frequency). If the value of any of C, V, or f are increased, the energy per second will increase eventually leading to increase in total energy and thereby improving the efficacy of disinfection. Capacitance (C) of a capacitor is fixed. Therefore, to increase energy by increasing the value of C, existing capacitor has to be replaced with a new capacitor having higher capacitance, which is generally expensive. Moreover, increasing the capacitance can increase the total energy only up to a certain extent.

Another approach for increasing the energy is to increase the value of pulse frequency f (i.e., the number of pulses per second generated by the pulse generator 150). However, the pulse frequency cannot be kept high for the entire operation cycle because increase in the value off increases the input current beyond the cutoff current which may lead to tripping of the circuit breaker 130. Yet another approach for increasing the energy is to increase the charging voltage V. However, the charging voltage (V) cannot be kept beyond a cutoff voltage for the entire operation cycle because it may lead to tripping of the circuit breaker 130. The cutoff voltage ($V_{th}$) may be defined as the maximum voltage applied across the capacitor 202 at which the operation cycle can be completed without tripping the circuit breaker 130. In other words, the cutoff voltage is the voltage across the capacitor 202 at or below which the circuit breaker 130 does not trip during the operation cycle.

Therefore, to increase the energy while avoiding the tripping of the circuit breaker 130, the controller 210 may vary the charging voltage momentarily between high and low values during the operation cycle. By combining a plurality of low, medium, and high voltage pulses (i.e., variable voltage amplitudes) in the operation cycle, it may be possible to increase the total energy per operation cycle. The combinations of variable voltage amplitudes may not change the average current significantly but can allow generation of few high energy pulses, mid energy pulses, and low energy pulses in each operation cycle. In addition, changing the value of V will have greater effect in overall increase in energy output since it has squared relation in equations (1) and (2). In other words, small increase in V would output large number to be multiplied to rest of the variables in the equations (1) and (2) resulting in more energy output and hence better disinfection.

In general, for an operational cycle, an output power (Po) delivered by the PUV device 120 is proportional to an input power (Pi) provided by the input source. i.e., $$Pi \propto Po$$

$$V_i * I_i \propto \frac{1}{2}CV^2 f$$

Since, input voltage of the input source is constant and capacitance of the capacitor 202 is also constant. Hence, the input current is directly proportional with frequency and voltage across the capacitor 202.

$$I_i \propto V^2 f$$

Any increase in the voltage across the capacitor 202 and the frequency may increase the input current across the circuit breaker 130 and may lead to tripping of the circuit breaker 130. The minimum voltage applied across the capacitor 202 at which the circuit breaker 130 trips without completing the operation cycle is referred as the cutoff voltage. The cutoff voltage may be determined by applying a constant voltage across the capacitor 202 during an entire operation cycle and the minimum voltage at which the circuit breaker trips is considered as the cutoff voltage.

In one non-limiting embodiment of the present disclosure, the controller 210 may generate a plurality of charging commands for charging the capacitor 202 during an operation cycle of the PUV device 120. The controller 210 may generate the plurality of charging commands by generating a plurality of variable voltage amplitudes for charging the capacitor 202 of the pulse generator 150. In general, a variable voltage amplitude is generated by allowing the capacitor 202 to charge to a desired voltage and once it reaches the desired voltage, the input to the capacitor 202 may be disconnected to stop the further charging of the capacitor 202. The controller 210 is programmed to generate the plurality of variable voltage amplitudes such that at least one of the generated voltage amplitudes is greater than the cutoff voltage amplitude.

In one non-limiting embodiment, the plurality of charging commands may comprise n sets of charging commands. Each set may comprise at least one charging command and may be associated with a particular charging interval and a particular voltage amplitude (i.e., all charging commands within a set may have the same voltage amplitude and the same charging interval).

In one non-limiting embodiment, the controller 210 may generate a plurality of discharging commands corresponding to the plurality of charging commands for discharging the capacitor. The capacitor may store energy while charging and releases the stored energy while discharging so as to produce pulsed energy signals. The pulsed energy signals may be provided to the germicidal lamp 160. The germicidal lamp 160 may generate UV pulses for disinfecting a subject. The various exemplary techniques of enhanced UV disinfection are explained below with the help of FIGS. 3(*a*)-(*d*), where voltage values are indicated along vertical axis and time values are indicated along horizontal axis.

In one non-limiting embodiment of the present disclosure, the controller 210 may generate the charging commands such that a time interval between any two consecutive/successive charging commands among the plurality of charging commands is same throughout the operation cycle. This time interval may be referred as "voltage pulse duration" in the present disclosure. Additionally, a voltage amplitude associated with one set of charging commands is different from a voltage amplitude associated with another set of charging commands. Hence, no two sets of charging commands have the same voltage amplitude, as illustrated in FIG. 3(*a*).

Referring now to FIG. 3(*a*), which shows an exemplary graph 300-1 illustrating variations in the voltage across the capacitor 202 for performing enhanced UV disinfection, in accordance with some embodiments of the present disclosure. For the sake of explanation, assume that the operation cycle of the PUV device 120 is T seconds and the cutoff voltage is Y1. Assuming that the controller 210 is programmed to generate three different types/sets of charging commands during the operation cycle. A first type of charging commands may have an associated first voltage amplitude X1, a second type of charging commands may have a second voltage amplitude Y1, and a third type of charging commands may have a third voltage amplitude Z1, where X1<Y1<Z1. However, each charging command of a particular type of charging commands may have a same voltage pulse duration (t). The controller 210 may be programmed to continuously generate charging commands of varying voltage amplitudes among X1, Y1, Z1 during the operation cycle each having the same voltage pulse duration (t).

For example, at the beginning of the operation cycle, the controller 210 may generate a first charging command for charging the capacitor 202. The first charging command may be generated by adjusting a voltage across the capacitor to 'X1' for charging the capacitor 202. The controller 210 may then charge the capacitor 202 up to the voltage amplitude X1. Consider that charging the capacitor 202 on the voltage amplitude X1 consumes 'O-a1' time duration i.e., the charging duration is 'O-a1'. Once the capacitor 202 is charged up to the voltage amplitude X1, the controller 210 may wait for a time period 'W1' before discharging the capacitor 202. The controller 210 may discharge the capacitor 202 after the lapse of waiting period W1. In another embodiment, the controller 210 may discharge the capacitor immediately once it reaches X1 and then wait for W1 time for generating the next charging command. Thus, in FIG. 3(*a*), the voltage pulse duration may also be referred as an interval between generation/issuance of two successive charging commands.

In one non-limiting embodiment, after discharging the capacitor, the controller 210 may generate a second charging command for charging the capacitor 202. The second charging command may be generated by adjusting a voltage across the capacitor to 'Y1' for charging the capacitor 202, where Y1>X1. The controller 210 may then charge the capacitor 202 up to the voltage amplitude Y1 for a charging duration of 'A1-b1'. Once the capacitor 202 is charged up to the voltage amplitude Y1, the controller 210 may wait for a time period 'W2' before discharging the capacitor 202. The controller 210 may discharge the capacitor 202 after the lapse of the waiting period (W2) to produce a medium energy pulse signal. In another embodiment, the controller 210 may discharge the capacitor immediately once it reaches Y1 and then wait for W2 time for generating the next charging command.

In one non-limiting embodiment, the controller 210 may then generate a third charging command for charging the capacitor 202. The third charging command may be generated by increasing a voltage amplitude across the capacitor to 'Z1' for charging the capacitor 202, where Z1>Y1. The controller 210 may then charge the capacitor 202 up to the voltage amplitude Z1 for a charging duration of 't' and discharge the capacitor 202 after the lapse of the voltage pulse duration (t) without any waiting interval to produce a high energy pulse signal.

It may be noted here that the value of charging interval is varying for different voltage amplitudes, but the value of voltage pulse duration is same (i.e., discharging is occurring at regular intervals). In general, higher the voltage amplitude, higher is the charging interval because the time required to charge the capacitor 202 increases. When the capacitor 202 is discharged after being charged using a particular voltage amplitude, it releases the stored energy and produces a pulsed energy signal. The pulsed energy signal may be provided to the germicidal lamp 160 which then generates UV pulses for disinfecting a subject.

In one non-limiting embodiment, the controller 210 may be programmed to continuously generate the charging and discharging commands of different voltage amplitudes among X1, Y1, and Z1 during the operation cycle. Thus, the germicidal lamp 160 continuously generates UV pulses for disinfecting the subject. It may be noted that since at least one charging voltage amplitude (e.g., Z1) of the plurality of voltage amplitudes (X1, Y1, Z1) is more than the cutoff voltage (e.g., Y1), the overall energy produced by using the variable voltages during the operation cycle is thousand folds more compared to energy produced by using a constant voltage during the same operation cycle thereby providing enhanced UV disinfection. Further, by providing the waiting/cooling period (e.g., W1, W2) between charging commands, tripping of the circuit breaker 130 may be prevented.

In the present disclosure, the term 'charging interval' or 'charging duration' is used within the context of its broadest definition. Specifically, charging interval of a capacitor may refer to the total time required for charging the capacitor when a particular voltage is applied across the capacitor. The value of charging interval may be different for different voltage amplitudes during an operation cycle.

In the present disclosure, the term 'voltage pulse interval' or 'voltage pulse duration' is used within the context of its broadest definition. Specifically, voltage pulse duration of a capacitor for a particular voltage is a time between two consecutive charging commands. The value of the voltage pulse duration may be same or different for different voltage amplitudes during an operation cycle.

In another non-limiting embodiment of the present disclosure, the controller 210 may utilize the waiting time as described in FIG. 3(*b*). The controller 210 may generate the charging commands such that a charging interval associated with one set of charging commands is different from a charging interval associated with another set of charging commands and a voltage amplitude associated with one set of charging commands is different from a voltage amplitude associated with another set of charging commands. Hence, no two sets of charging commands have the same voltage amplitude and same charging interval, as illustrated in FIG. 3(*b*).

Referring now to FIG. 3(*b*), which shows another exemplary graph 300-2 illustrating variations in the voltage across the capacitor 202 for performing enhanced IN disinfection, in accordance with some embodiments of the present disclosure. For the sake of explanation, assume that the operation cycle of the PUV device is T seconds and the cutoff voltage is Y2. Assuming that the controller 210 is programmed to generate three different types of charging commands during the operation cycle having voltage amplitudes X2, Y2, and Z2 respectively, where X2<Y2<Z2. It may be noted that a charging time of commands having a particular voltage amplitude is same. Further, the charging time of commands having the particular voltage amplitude is different from a charging time of commands having another particular voltage amplitude. Also, the charging time and voltage pulse duration of commands having a particular voltage amplitude may be same throughout the operation cycle. The controller 210 may be programmed to continuously generate charging commands of varying voltage amplitudes among X2, Y2, Z2 during the operation cycle.

For example, the controller 210 may generate a first charging command for charging the capacitor 202. The first charging command may be generated by adjusting a voltage amplitude of across the capacitor 202 to X2 for charging the capacitor 202. The controller 210 may then charge the capacitor 202 up to the voltage amplitude X2. Consider that the charging time for charging the capacitor 202 on the voltage amplitude X2 is 't1'. Once the capacitor 202 is charged up to the voltage amplitude X1, the controller 210 may immediately discharge the capacitor 202 without waiting for any time interval to produce an energy pulse i.e., discharging command is generated/issued as soon as the voltage amplitude across the capacitor 202 reaches the voltage amplitude 'X2'.

After discharging the capacitor, the controller 210 may issue/generate a next charging command for charging the capacitor 202 by adjusting a voltage across the capacitor 202 to any voltage amplitude among X2, Y2, Z2 for charging the capacitor 202. The controller 210 may then charge the capacitor 202 up to the adjusted voltage amplitude and once the capacitor 202 is charged up to the adjusted voltage amplitude, the controller 210 may immediately discharge the capacitor 202 to produce another energy pulse, as shown in FIG. 3(*b*).

When the capacitor 202 is discharged after being charged using a particular voltage amplitude, it releases the stored energy and produces a pulsed energy signal. The pulsed energy signal may be provided to the germicidal lamp 160 which then generates UV pulses for disinfecting a subject. The controller is programmed to continuously generate the charging of different voltage amplitudes among X2, Y2, and Z2 and discharging commands during the operation cycle. Thus, the germicidal lamp 160 continuously generates UV pulses for disinfecting the subject.

In yet another non-limiting embodiment of the present disclosure, the operation cycle of the PUV device 120 may be divided into a plurality of sub-operation cycles. Each sub-operation cycle of the plurality of sub-operation cycles may comprise one or more charging commands having the same charging interval and the same voltage amplitude, as illustrated in FIG. 3(*c*).

Referring now to FIG. 3(*c*), which shows another exemplary graph 300-3 illustrating variations in the voltage across the capacitor 202 for performing enhanced UV disinfection, in accordance with some embodiments of the present disclosure. For the sake of explanation, assume that the operation cycle of the PUV device is T seconds and the cutoff voltage amplitude is Y3. Consider that the operation cycle is divided into three sub-operation cycles each of T3 duration. Assuming that the controller 210 is programmed to generate three different types of charging commands during the operation cycle having voltage amplitudes X3, Y3, and Z3 respectively, where X3<Y3<Z3. It may be noted that a charging time of commands having a particular voltage amplitude is same. Further, the charging time of commands having the particular voltage amplitude is different from a charging time of commands having another particular voltage amplitude. Also, the charging time and voltage pulse duration of commands having a particular voltage amplitude may be same throughout the operation cycle.

The controller 210 may generate a plurality of a first type of charging commands during the first sub-operation cycle for charging the capacitor 202. Each of the plurality of first type of charging commands may be generated by adjusting a voltage amplitude across the capacitor 202 to X3 for charging the capacitor 202. For each of the plurality of first type of charging commands, the controller 210 may charge the capacitor 202 up to the voltage amplitude X3 and once the capacitor 202 is charged, immediately discharge the capacitor 202 to produce an energy pulse. This way multiple energy pulses of same energy are produced during the first sub-operation cycle. The charging interval of each charging command within the first sub-operation cycle may be same.

During a second sub-operation cycles, the controller 210 may generate a plurality of second type of charging commands for charging the capacitor 202 by adjusting a voltage amplitude across the capacitor 202 to Y3 for charging the capacitor 202. Similarly, during a third sub-operation cycles, the controller 210 may generate a plurality of third type of charging commands for charging the capacitor 202 by adjusting a voltage amplitude across the capacitor 202 to Z3 for charging the capacitor 202. For each charging commands of any type, the controller 210 may charge the capacitor 202 up to the adjusted voltage amplitude and once the capacitor 202 is charged, immediately discharge the capacitor 202 to produce an energy pulse.

The controller 210 may be programmed to continuously generate a particular type of charging commands of voltage amplitudes among X3, Y3, or Z3 during each sub-operation cycle of the operation cycle. Thus, the germicidal lamp 160 continuously generates UV pulses for disinfecting the subject.

In one non-limiting embodiment, depending on voltage amplitudes, a number of charging commands (i.e., pulse frequency) during one sub-operation cycle having a plurality of one type of charging commands may be different from a number of charging commands during another sub-operation cycle having a plurality of another type of charging commands. For example, the plurality of third type of charging commands during the third sub-operation cycle may be less than the plurality of second type of charging commands during the second sub-operation cycle. Similarly, the plurality of second type of charging commands during the second sub-operation cycle may be less than the plurality of first type of charging commands during the first sub-operation cycle.

In yet another non-limiting embodiment of the present disclosure, the operation cycle of the PUV device 120 may be divided into a plurality of sub-operation cycles. Each sub-operation cycle of the plurality of sub-operation cycles may comprise one or more charging commands having one or more voltage amplitudes, as illustrated in FIG. 3(*d*).

Referring now to FIG. 3(*d*), which shows another exemplary graph 300-4 illustrating variations in the voltage across the capacitor 202 for performing enhanced IN disinfection, in accordance with some embodiments of the present disclosure. For the sake of explanation, assume that the operation cycle of the PUV device is T seconds and the cutoff voltage amplitude is Y4. Consider that the operation cycle is divided into two sub-operation cycles each of T4 duration. Assuming that the controller 210 is programmed to generate three different types of charging commands during the operation cycle having voltage amplitudes X4, Y4, and Z4 respectively, where X4<Y4<Z4. It may be noted that a charging time of commands having a particular voltage amplitude is same. Further, the charging time of commands having the particular voltage amplitude is different from a charging time of commands having another particular voltage amplitude. Also, the charging time and voltage pulse duration of commands having a particular voltage amplitude may be same throughout the operation cycle.

During each sub-operation cycle, the controller 210 may generate a plurality of charging commands having voltage amplitudes among X4, Y4, and Z4 for charging the capacitor 202. Also, the number of charging commands in one sub-operation cycle may be same or different from the number of charging commands in another sub-operation cycle. For example, in exemplary illustration of FIG. 3(*d*), the controller 210 generates a total of 6 charging commands during the first sub-operation cycle (3 commands of voltage amplitude X4, 2 commands of voltage amplitude Y4, and 1 command of voltage amplitude Z4). Further, the controller 210 generates a total of 7 charging commands during the second sub-operation cycle (5 commands of voltage amplitude X4, 1 command of voltage amplitude Y4, and 1 command of voltage amplitude Z4). In one non-limiting embodiment, a sub-operation cycle of the plurality of sub-operation cycles may have charging command each having the same voltage amplitude. For example, the first sub-operation cycle may comprise charging commands each having same voltage amplitude (i.e., X4 or Y4 or Z4).

For each charging commands, the controller 210 may charge the capacitor 202 up to the specified voltage amplitude and once the capacitor 202 is charged, immediately discharge the capacitor 202 to produce energy pulses which may be provided to the germicidal lamp 160 for disinfecting a subject.

In one non-limiting embodiment of the present disclosure, the controller 210 may be configured to reduce the pulse frequency during an operation/sub-operation cycle in response to detecting that current across the circuit breaker 130 is exceeding the cutoff current of the circuit breaker 130. For example, in the embodiment of FIG. 3(*c*), upon detecting that the current across the circuit breaker 130 is exceeding the cutoff current, the controller 210 may reduce the pulse frequency during at least one sub-operation cycle by introducing at least one waiting/cooling interval in between one or more charging intervals. For instance, to reduce the pulse frequency during the first sub-operation cycle of FIG. 3(*c*), the controller 210 may introduce a waiting interval after each charging interval, or after two charging intervals, or at the end of the first sub-operation cycle, and like.

In one non-limiting embodiment of the present disclosure, the system 100 may comprises a current sensor (not shown) before the circuit breaker 130. The current sensor may continuously measure a value of the input current and send the measured value to the PUV device 120 using wired or wireless communication. The wireless communication between the PUV device 120 and the current sensor may be facilitated using a network known in the art or developed later. For example, the network may comprise a data network such as, but not restricted to, the Internet, Local Area Network (LAN), Wide Area Network (WAN), Metropolitan Area Network (MAN), etc. In certain embodiments, the network may include a wireless network, such as, but not restricted to, a cellular network and may employ various technologies including Enhanced Data rates for Global Evolution (EDGE), General Packet Radio Service (GPRS), Global System for Mobile Communications (GSM), Internet protocol Multimedia Subsystem (IMS), Universal Mobile Telecommunications System (UMTS), 3G, 4G, 5G etc. In one embodiment, the network may include or otherwise cover networks or subnetworks, each of which may include, for example, a wired or wireless data pathway.

In one embodiment, the controller 210 of the PUV device 120 may dynamically adjust the voltage across the capacitor 202 based on the inputs received from the current sensor to avoid tripping of the circuit breaker 130.

In one non-limiting embodiment, the memory 204 may store a model which may be trained based on historical data (e.g., data from previous operation cycles including historical values of currents, voltages, frequencies, tripping data etc.). The controller 210 may be configured to use the trained model for generating the plurality of voltage amplitudes for charging the capacitor 202. In one non-limiting embodiment of the present disclosure, the controller 210 may use the trained model for increasing/decreasing the pulse frequency during the operation/sub-operation cycle and for changing the pattern of the plurality of voltage amplitudes in real time.

In one non-limiting embodiment of the present disclosure, the controller 210 may take into account the other devices 140 electrically connected with the input source 110 while adjusting the voltage across the capacitor. In one non-limiting embodiment, a separate circuit breaker 130 and current sensor may be provided inside the PUV device 120.

It may be noted that the voltage graphs shown in FIGS. 3(*a*)-3(*d*) are for illustrative purpose only. In the illustrative examples of FIGS. 3(*a*)-3(*d*) only three distinct voltage amplitudes (X1, Y1, Z1) are shown. However, the present disclosure is not limited thereto and, in general, any number of distinct voltage amplitudes in any order may be generated during the operation cycle. Further, the duration of the operation cycle for different types of surfaces/subjects may be different. A surface/subject may require more than one operation cycles for disinfection.

Since at least one charging voltage amplitude from the plurality of variable voltage amplitudes is more than the cutoff voltage, the overall energy produced by using the variable voltages during the operation cycle is thousand folds more compared to energy produced by using a constant voltage during the same operation cycle thereby, providing enhanced UV disinfection, as illustrated below.

Consider an example, where the PUV device 120 is run for 15 minutes (i.e., operation cycle is of 15 minutes) at a pulse frequency of 16 Hz. Consider that the capacitance of capacitor is 16 μF and a constant voltage applied across the capacitor during the operation cycle is 2200V. By putting these values in equation (3), the total energy output of the PUV device for the entire operation cycle is:

$$E_1 = (0.5*16*2200*2200*16*15*60)/10^6$$

$$E_1 = 557568\,J.$$

Consider another example, where the PUV device 120 is run for 15 minutes at a pulse frequency of 16 Hz. Consider that the capacitance of capacitor is 16 μF and three different variable voltages (2000V, 2200V, 2600V) are applied across the capacitor each for 5 minutes during the entire operation cycle. By putting these values in equation (3), the total energy output by the PUV device for the operation cycle is:

$$E_2 = (0.5*16*(2000*2000+2200*2200+2600*2600)*16*5*60)/10^6$$

$$E_2 = 599040\,J.$$

Hence, it is clear from above that the energy output by the PUV device when using variable voltage amplitudes is much higher than the energy output by the PUV device when using a constant voltage amplitude.

Figure 4:
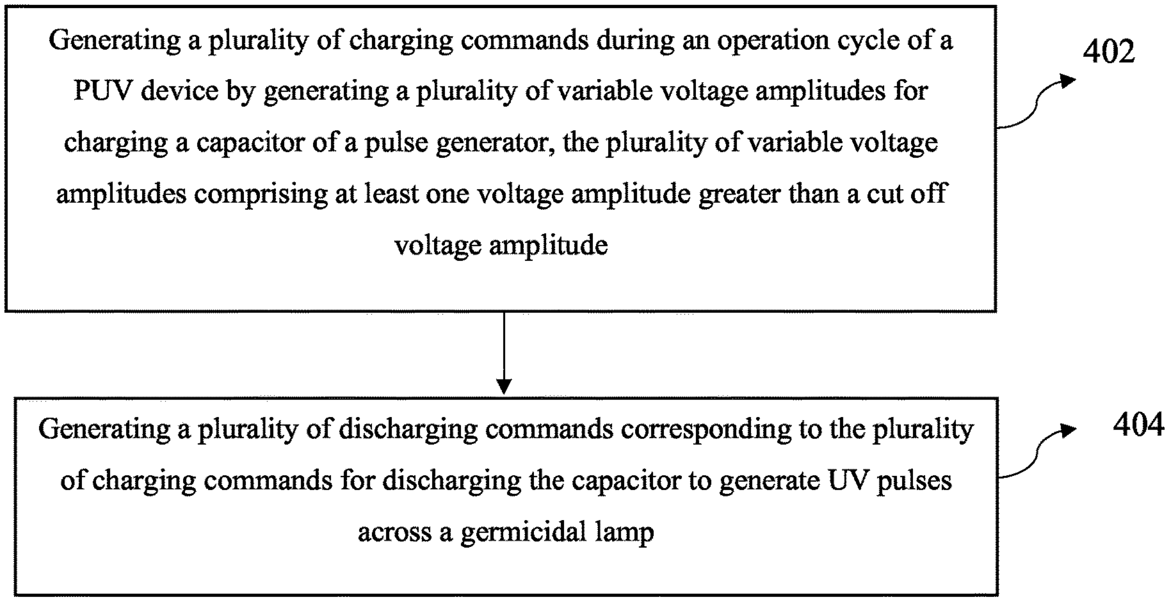
FIG. 4 depicts a flowchart 400 illustrating a method of operating the PUV device, in accordance with some embodiments of the present disclosure.

Referring now to FIG. 4, a flowchart is described illustrating an exemplary method 400 of operating a pulsed ultraviolet (PUV) device 150 comprising a pulse generator and a germicidal lamp, according to an embodiment of the present disclosure. The method 400 is merely provided for exemplary purposes, and embodiments are intended to include or otherwise cover any methods or procedures for operating the PUV device.

The method 400 may include, at block 402, generating a plurality of charging commands during an operation cycle of the PUV device 120. The generating of the plurality of charging commands may comprise generating a plurality of variable voltage amplitudes for charging a capacitor 202 of the pulse generator 150. The plurality of variable voltage amplitudes may comprise at least one voltage amplitude greater than a cut off voltage amplitude. For example, the controller 210 of FIG. 2 may be configured to generate the plurality of charging commands during the operation cycle of the PUV device 120.

At block 404, the method 400 may include generating a plurality of discharging commands corresponding to the plurality of charging commands for discharging the capacitor to generate IN pulses across the germicidal lamp. For example, the controller 210 of FIG. 2 may be configured to generate the plurality of discharging commands corresponding to the plurality of charging commands for discharging the capacitor to generate IN pulses across the germicidal lamp.

In one non-limiting embodiment of the present disclosure, the plurality of charging commands may comprise n sets of charging commands, each set comprising at least one charging command. Each set of the n sets of charging commands may be associated with a particular charging interval and a particular voltage amplitude.

In one non-limiting embodiment of the present disclosure, a time interval between any two consecutive charging commands among the plurality of charging commands is same during the operation cycle, and a voltage amplitude associated with one set of charging commands is different from a voltage amplitude associated with another set of charging commands.

In one non-limiting embodiment of the present disclosure, a charging interval associated with one set of charging commands is different from a charging interval associated with another set of charging commands, and a voltage amplitude associated with one set of charging commands is different from a voltage amplitude associated with another set of charging commands.

In one non-limiting embodiment of the present disclosure, the operation cycle of the PUV device may comprise n sub-operation cycles. Each sub-operation cycle of the n sub-operation cycles may comprise one or more charging commands having the same charging interval and the same voltage amplitude.

In one non-limiting embodiment of the present disclosure, the cut-off voltage is the voltage below which a circuit breaker electrically connected between an input source and the pulse generator does not trip.

The above method 400 may be described in the general context of computer executable instructions. Generally, computer executable instructions can include routines, programs, objects, components, data structures, procedures, modules, and functions, which perform specific functions or implement specific abstract data types. In one aspect, the method 400 may be performed by an apparatus at least comprising a processor and a memory.

According to certain embodiments, the device and method of the present disclosure may allow a user (or anyone) to customize the settings of the PUV device to meet the disinfection criteria of different objects, such as food, utensils, packaging, etc. without changing the electronic components of the system. The method and device of the present disclosure may be applied in a broad range of applications, such as disinfecting food packaging, food products, produce, pet food, household utensils, countertop surfaces, furniture surfaces, water, air, and so on.

The order in which the various operations of the method are described is not intended to be construed as a limitation, and any number of the described method blocks can be combined in any order to implement the method. Additionally, individual blocks may be deleted from the method without departing from the spirit and scope of the subject matter described herein. Furthermore, the methods can be implemented in any suitable hardware, software, firmware, or combination thereof.

The various operations of methods described above may be performed by any suitable means capable of performing the corresponding functions. The means may include various hardware and/or software component(s) and/or module(s), including, but not limited to the controlling means, generating means, storing means etc. Generally, where there are operations illustrated in Figures, those operations may have corresponding counterpart means-plus-function components.

It may be noted here that the subject matter of some or all embodiments described with reference to FIGS. 1-3 may be relevant for the method and the same is not repeated for the sake of brevity.

In a non-limiting embodiment of the present disclosure, one or more non-transitory computer-readable media may be utilized for implementing the embodiments consistent with the present disclosure. A computer-readable media refers to any type of physical memory (such as the memory 206) on which information or data readable by a processor or controller may be stored. Thus, a computer-readable media may store one or more instructions for execution by the controller 210, including instructions for causing the at controller 210 to perform steps or stages consistent with the embodiments described herein. The term "computer-readable media" should be understood to include tangible items and exclude carrier waves and transient signals. By way of example, and not limitation, such computer-readable media can comprise Random Access Memory (RAM), Read-Only Memory (ROM), volatile memory, nonvolatile memory, hard drives, Compact Disc (CD) ROMs, Digital Video Disc (DVDs), flash drives, disks, and any other known physical storage media.

Thus, certain aspects may comprise a computer program product for performing the operations presented herein. For example, such a computer program product may comprise a computer readable media having instructions stored (and/or encoded) thereon, the instructions being executable by one or more processors or controllers to perform the operations described herein. For certain aspects, the computer program product may include packaging material.

The various illustrative logical blocks, modules, and operations described in connection with the present disclosure may be implemented or performed with a general-purpose processor, a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A general-purpose processor may include a microprocessor, but in the alternative, the processor may include any commercially available processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

The terms "including", "comprising", "having" and variations thereof mean "including but not limited to", unless expressly specified otherwise.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the embodiments of the present invention are intended to be illustrative, but not limiting, of the scope of the invention, which is set forth in the appended claims.

What is claimed is:

1. A method of operating a pulsed ultraviolet (PUV) device comprising a pulse generator and a germicidal lamp, the method comprising:

generating a plurality of charging commands during an operation cycle of the PUV device, wherein the generating the plurality of charging commands comprises generating a plurality of variable voltage amplitudes for charging a capacitor of the pulse generator, and wherein the plurality of variable voltage amplitudes comprises at least one voltage amplitude greater than a cut off voltage amplitude; and generating a plurality of discharging commands corresponding to the plurality of charging commands for discharging the capacitor to generate UV pulses across the germicidal lamp, wherein the plurality of charging commands comprises n sets of charging commands, each set comprising at least one charging command, and wherein each set of the n sets of charging commands is associated with a particular charging interval and a particular voltage amplitude, wherein a time interval between any two consecutive charging commands among the plurality of charging commands is same during the operation cycle, and wherein a voltage amplitude associated with one set of charging commands is different from a voltage amplitude associated with another set of charging commands.

2. The method of claim 1, wherein a charging interval associated with one set of charging commands is different from a charging interval associated with another set of charging commands, and wherein a voltage amplitude associated with one set of charging commands is different from a voltage amplitude associated with another set of charging commands.

3. The method of claim 1, wherein the operation cycle of the PUV device comprises n sub-operation cycles, and wherein each sub-operation cycle of the n sub-operation cycles comprises one or more charging commands having the same charging interval and the same voltage amplitude.

4. The method of claim 1, wherein the cut off voltage amplitude is the maximum voltage amplitude below which a circuit breaker electrically connected between an input source and the pulse generator does not trip.

* * * * *